United States Patent [19]

Dinzburg

[11] Patent Number: 5,178,017
[45] Date of Patent: Jan. 12, 1993

[54] TEST FIXTURE FOR MEASURING STIFFNESS IN FLEXIBLE MATERIALS

[75] Inventor: Boris Dinzburg, Niles, Ill.

[73] Assignee: Chicago Rawhide Manufacturing Company, Elgin, Ill.

[21] Appl. No.: 767,401

[22] Filed: Sep. 30, 1991

[51] Int. Cl.⁵ ............................................. G01N 3/20
[52] U.S. Cl. ..................................................... 73/849
[58] Field of Search ................. 73/789, 849, 850, 851, 73/852

[56] References Cited

U.S. PATENT DOCUMENTS

| | | | |
|---|---|---|---|
| 2,506,048 | 5/1950 | Van Den Akker | 73/852 |
| 3,194,063 | 7/1965 | McKean | 73/852 X |
| 3,500,679 | 3/1970 | Smith | 73/850 |
| 4,730,498 | 3/1988 | Blanch | 73/852 |

Primary Examiner—Jerry W. Myracle
Attorney, Agent, or Firm—Lockwood, Alex, FitzGibbon & Cummings

[57] ABSTRACT

A test fixture apparatus for measuring the bending stiffness of specimens of flexible materials such as elastomers and like polymers. The preferred form includes two elements, an anvil member and a yoke member. The yoke includes a crosspiece and two pairs of depending legs forming parallel, spaced apart, inverted "V"s. Rollers extend between points on the lower parts of the legs to support the test specimens. The anvil member includes a crosspiece and a single pair of arms positioning a roller for applying a downward load to the center of the specimen held on the yoke rollers. The rollers allow the surface-soft specimens to slide over rather than dig into their supports, and this provides more accurate, repeatable readings of the bending forces applied to the specimens.

16 Claims, 2 Drawing Sheets

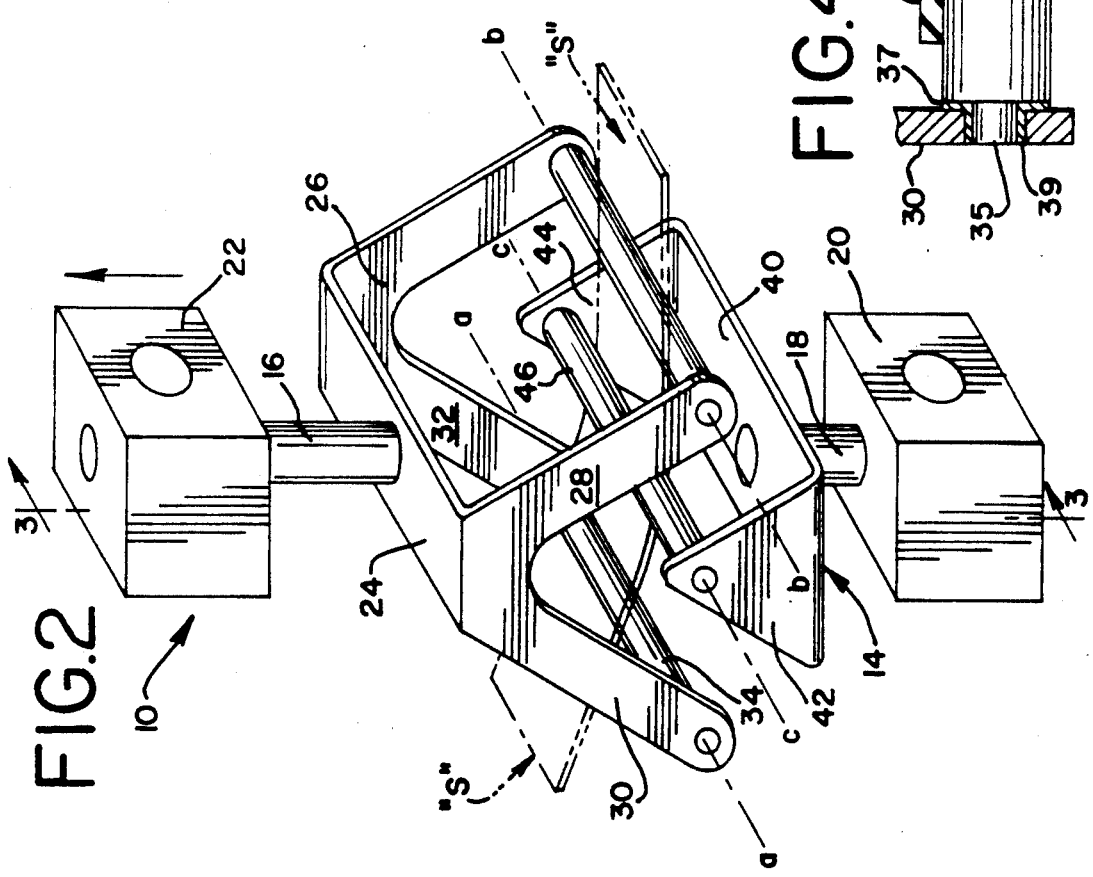
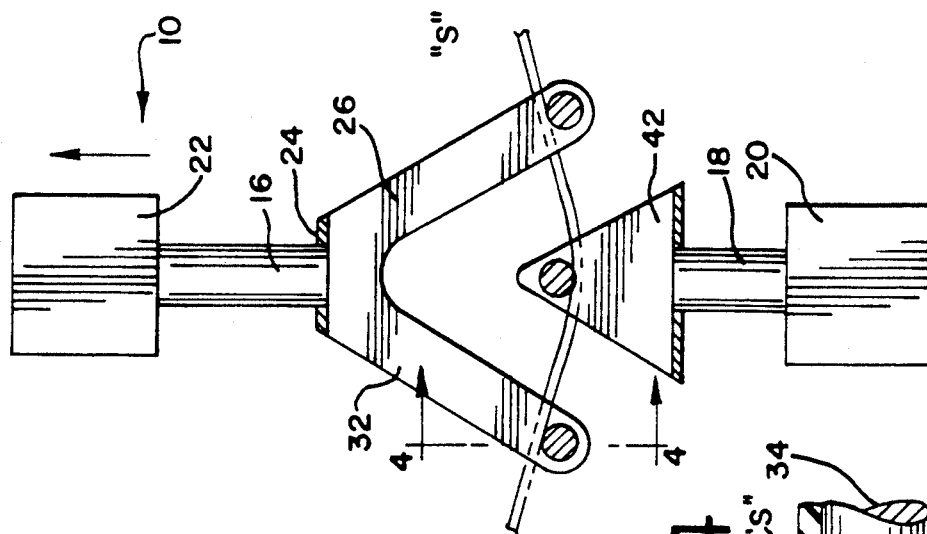
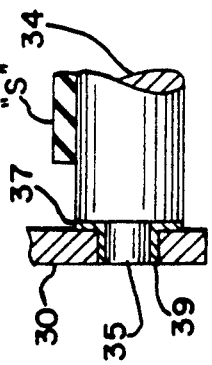

TEST FIXTURE FOR MEASURING STIFFNESS IN FLEXIBLE MATERIALS

BACKGROUND AND BRIEF DESCRIPTION

The present invention relates generally to devices for testing materials. More specifically, the present invention relates to an improved apparatus for a more reliable and accurate manner for measuring the bending stiffness of flexible materials such as synthetic elastomers and other rubber-like materials. The apparatus is adopted for use in a tension-compression testing device such as an "Instron" force/deflection tester, sometimes referred to herein for simplicity merely as a "tensiometer".

The test fixture of the invention includes a yoke portion positioning a pair of identical, material-engaging support units and an anvil portion including a single, material engaging unit forming its "nose" portion. In use, a sheet of flexible material is placed in spanwise relation above the support units of the yoke with the sheet extending under the nose of the anvil. When the yoke and anvil are respectively attached to the relatively movable elements of a conventional tensiometer, the bending stiffness of a particular material specimen can be measured. The provision of rotatable, specimen-engaging supports allows the material specimen to advance smoothly over the support rollers as it deflects under a pull from the nose portion; the rolling action prevents the specimen from binding or grabbing one or both of its support elements during measurement of bending stiffness.

By way of background, various devices and methods are known for testing the physical properties of a wide range of materials. Today, wide ranges of materials are tested for structural strength in various ways, and the test results are then used to classify the materials as to a particular property. Properties such as bulk modulus, compressive strength, tensile strength, shear strength, stiffness in bending, elasticity and other properties are routinely tested for.

Many structural materials may be broadly characterized as being low deformation materials. These low deformation materials include metals and hard plastics. These are considered "low deformation" because they show relatively slight deformation under a given force. Devices for testing these low deformation materials have typically included attachments for bending or flexure testing, using a compression load cell in a conventional tensiometer. Such structural and semi-structural materials include metals, alloys, hard plastics, chip board, particle board and the like. Tests of these materials commonly use a three- or four-point compression loading method to determine stress/strain values throughout a range appropriate for the materials tested. The test fixtures work well and give accurate, repeatable readings with these materials.

Conventional test fixtures have typically been unsatisfactory for certain kinds of testing done on softer materials, such as rubber-like materials and flexible polymers. Where only the "stretchability" or extension/contraction, hysteresis and ultimate tensile strength or yield point of such soft materials are in question, appropriate fixtures are sometimes available. These tests can and do accurately reflect certain properties of materials with greater or less accuracy.

In recent years, however, materials such as elastomers have begun to be used in other structural applications, i.e., in areas wherein the properties of stiffness in bending, for example, are of concern. Since the materials are soft, the absolute values are relatively low, and accuracy of measurement during testing is therefore of great importance.

A poorly designed test fixture is one which permits or encourages erratic or inaccurate readings. In measuring the stiffness of flexible materials of low modulus, available equipment has typically required that the material be inserted in a test fixture and tested in the same manner as harder, low deformation materials. For tests of harder materials, the test fixture usually included specimen support points or bars with sharp edges. While surface-hard materials are not affected by such fixtures, when softer materials are placed on such supports, surface engagement between fixture and specimen may cause grabbing or holding of the materials when bending stiffness is being measured. This introduces error into the bending stiffness measurement, either in absolute terms or in erratic, non-repeatable observations. The difficulty with proper observation is aggravated where the bending tests involve specimen deflection that is "seen" by the instrument as extension or tensioning of the specimen.

The present invention overcomes the aforementioned problems and difficulties in the prior art by providing an apparatus for measuring the stiffness of softer materials especially surface-soft materials, in bending. The apparatus incorporates a specialized anvil and yoke member for use with a conventional tensiometer. Both the yoke and the anvil are equipped with specimen-engaging cylindrical rollers at the point of specimen contact. Using this fixture, the required bending force supplied to the materials being tested can be accurately assessed. The cylindrical supports have a substantially circular cross-section, and are mounted relative to the yoke and the anvil using low-friction means such as ball bearings or bushing to allow the rollers to rotate freely about their longitudinal axes. In this manner, a material such as a rubber or other flexible material can be tested for stiffness in bending without undesirably introducing another force or term, i.e., tensioning of the specimen as a whole, to the measurement. As pointed out, if there is a problem of the support grabbing the specimen, it is almost certain that the specimen material will stretch or extend as it undergoes bending.

The rotatable supports eliminate the grabbing associated with prior art devices for such surface-soft materials, since rotation of the supports allows the sheet of material to advance over the supports under the load applied by the anvil and its associated loading nose. This provides a nearly frictionless surface to support the sheet of material while the bending stiffness measurement is being taken. In the preferred embodiment, the apparatus is provided as a three point flexural attachment to a conventional tensiometer wherein all three specimen-engaging elements are cylindrical rollers.

In view of the failure of the prior art to provide a fully satisfactory test fixture, it is an object of the invention to provide an improved test fixture apparatus for the measurement of bending stiffness characterizing certain materials with soft surfaces.

Another object of the invention is to provide a test fixture that provides improved accuracy when measuring the stiffness of specimens of certain surface-soft materials under an applied bending movement.

A further object of the present invention is to provide a test fixture for measuring stiffness of certain soft materials wherein the test fixture includes low friction, cylindrical supports to allow for test specimens to ride over the support rather than being grabbed by the support so as to create false or erratic readings.

A still further object of the invention is to provide a test fixture which is adaptable for use with existing tensiometers or other test devices.

A further object of the invention is to provide a low-cost test apparatus which is easy to manufacture and which is reliable in use.

Another object of the invention is to provide a test fixture apparatus for determining the bending stiffness of a specimen having a soft surface wherein the forces imparted to the specimen are transmitted through cylindrical elements that are free to rotate about their own axes so as to minimize or eliminate the effect of frictional contact between the surface of the specimen and a supporting surface of the test fixture.

Another object of the invention is to provide a test fixture apparatus which retains its advantages even if made in different sizes to accommodate test specimens.

Yet another object of the invention is to provide a simple and inexpensive test fixture using rotatable contacts or supports for a specimen and which is capable of determining bending stiffness and other properties of test specimens of a wide variety of materials having soft exterior surfaces.

Another object of the invention is to provide a test fixture which is self-centering in operation and requires little, if any, calibration for effective use.

The foregoing and other objects and advantages are achieved by providing a test fixture for measuring the bending stiffness of a specimen of flexible material having soft exterior surfaces, the test member including a yoke member and an anvil member each including legs arranged in pairs and adapted to support rotatable contact elements which, in position of use, respectively support a test specimen from below and engage it from above so as to impart a measurable bending movement to the specimen as the anvil and yoke move relative to each other.

The manner in which the foregoing and other objects and advantages are achieved in practice will become more clearly apparent when reference is made to the following detailed description of the preferred embodiments of the invention set forth by way of example and shown in the accompanying drawings, wherein like reference numbers indicate corresponding parts throughout.

BRIEF DESCRIPTION OF THE DRAWINGS

FIG. 2 is an enlarged perspective view of the test apparatus for measuring stiffness of soft materials and constructed in accordance with the principles of the present invention; and FIG. 3 is a vertical sectional view of the test fixture of FIG. 1, taken along the lines 2—2 thereof; and FIG. 4 is an enlarged fragmentary section view of the apparatus of FIG. 3, taken along lines 4—4 thereof.

DESCRIPTION OF THE PREFERRED EMBODIMENTS OF THE INVENTION

Figure 1:
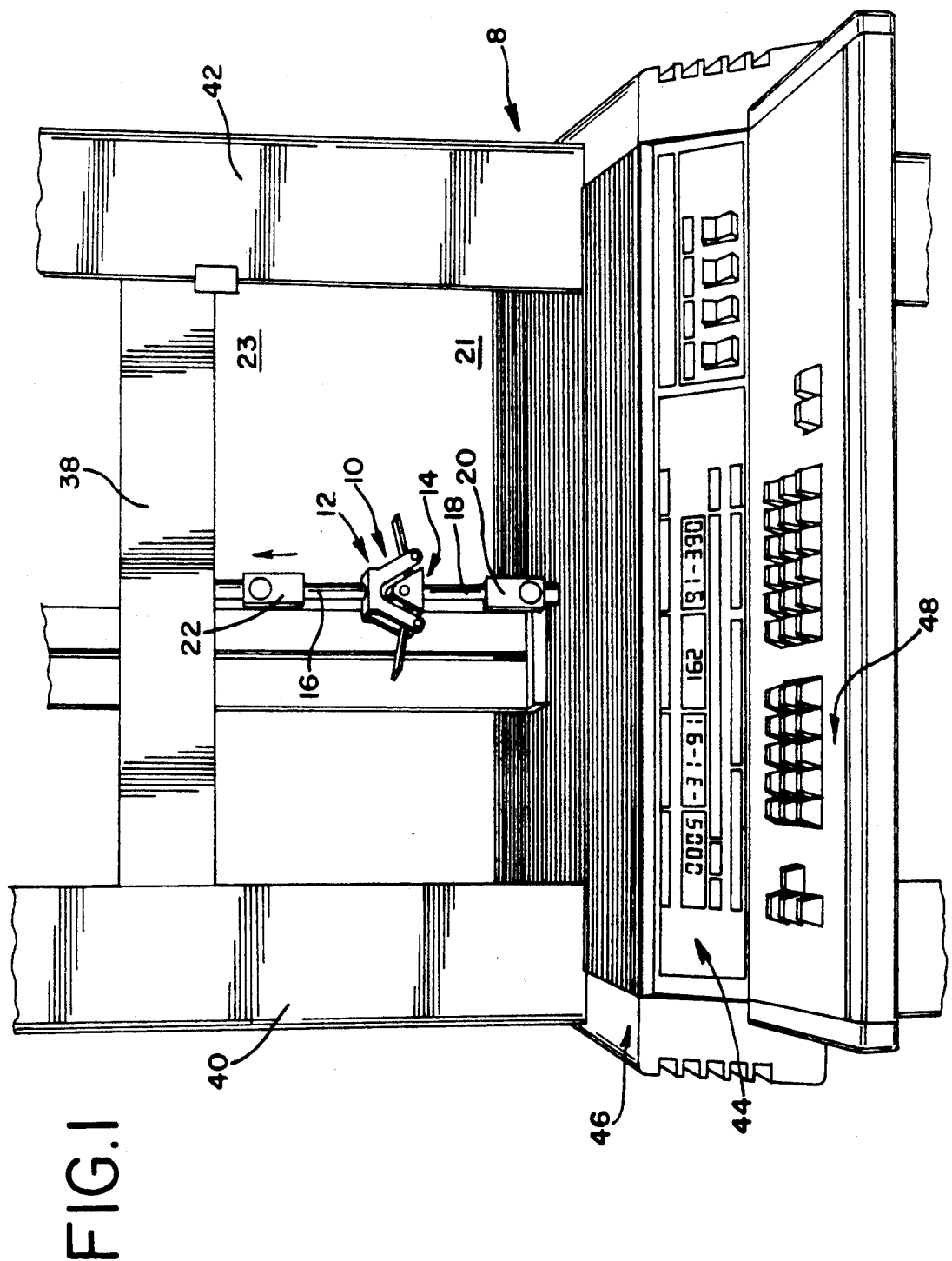
FIG. 1 is a perspective view of a test fixture embodying the invention, showing the fixture positioned within a tensiometer and further showing a specimen positioned between portions of the test fixture.

Whereas the invention may be embodied in somewhat different forms, and may be varied somewhat in dimensions, as well as exact configuration, and although the preferred forms of testing fixture of the apparatus may have individual parts constructed and arranged so as to test particular sizes and shapes of specimens, a description of one preferred form of invention will be given wherein a tensiometer is a conventional unit, the specimen support fixture or yoke is the upper element, the downforce applying member is an anvil or single or contact element unit, and wherein each includes means for direct attachment to an associate static point or load cell as the case may be.

Referring now to the drawings in detail, FIGS. 1 and 2 show a test fixture apparatus generally designated 10, constructed so as to embody the principles of the invention. The test fixture 10 includes two principle elements, the yoke element generally designated 12 and an anvil element generally designated 14. As will appear, a test specimen "S" is positioned by the test fixture for measurement of stiffness in bending.

The yoke member 12 is supported relative to a static point 22 by a vertically extending shaft 16, while a counterpart shaft 18 extends downwardly from the anvil member 14 and is joined to a load cell 20. Suitable connections are made between the static point 22 for the shaft 16 and the between the load cell 20 and the lower shaft 18, so that proper alignment can be achieved. In this connection, it will be appreciated that it is customary for the load to be determined through the use of one load cell 20 which provides an output signal translatable into a reading for a visible scale or for display and recording by a pen or the like. Customarily, one connection to one of the test fixtures is made at what is termed a static point, that is, a comparatively immovable, non-instrumented point. Whether or not such point actually moves is immaterial, the expression "static" merely meaning that it does not intentionally deflect as a part of the load measuring process. On the other hand, the load cell contains its own known means, such as a force transducer, for generating a characteristic electrical signal proportionately responsive to the degree of applied force. It is therefore assumed that only one load cell is used but this is not an important feature of the invention.

Referring now to the yoke member 12, this unit will be seen to include a cross-piece 24, having two pairs of spaced apart legs 26, 28, 30, 32, extending downwardly therefrom. The complementary leg pair 26, 28 is arranged in a downwardly open, V-configuration relative to the leg pair 30, 32. All of the legs 26–32 are vertical, and the legs 26, 28 are spaced apart each other the same amount as are their counterparts 30, 32 in the other pair.

Referring now to another important element of the yoke member, a pair of spaced apart specimen support rollers 34, 36 are provided and are arranged as shown. The rollers 34, 36 are mounted for free rotation about their respective longitudinal axes a-a, b-b. As shown in FIG. 4, a typical roller 34 includes a reduced diameter section 35 forming its end portion, and this end 35 is received within a bushing 37 made from a low friction material. The bushing is, in turn, received in an opening 39 in the leg 32 of the yoke member 12. This arrangement provides for minimum friction, it being understood that the bushing may be made from a suitable low-friction material such as a fluorocarbon or a bronze material, for example. Other alternatives such as needle or ball bearing mountings may be provided if indicated by the specimen size or other considerations.

Referring now to the other main element, the anvil member 14, this unit is shown likewise to include a horizontal crosspiece 40 and a pair of vertically extending legs 42, 44 of triangular section in elevation. Specimen-engaging means are provided in the form of a nose roller 46 extending between the legs 42, 44. Although not shown in detail, it will be understood that the nose roller 46 may have reduced diameter end portions journaled for rotation relative to the leg 42 by means of a low friction arrangement such as that provided for roller 34 and illustrated in FIG. 4. Other suitable arrangements may be made for mounting the roller 46.

In this connection, there are cases wherein the nose roller will be called upon to move about its rotational axis c-c (FIG. 2). This may occur in the event of an off-center loading or an irregular deformation of the specimen. In addition, any initial misalignment in parts may be resolved by permitting slight rotational movement of the nose roller 46 as the specimen is engaged. This prevents tensioning a specimen which is only intended to be stressed in bending.

Referring now to the use of the inventive test fixture, such use is made in keeping with familiar principles. For purposes of illustration, a flexible specimen "S" of a moderately soft rubber, such as a 60 durometer rubber specimen of four inch length, two inch width and $\frac{1}{8}$" thickness, may be positioned as shown in FIGS. 2 and 3. As initially positioned, the specimen "S" will span the rollers 34, 36, and show little, if any, initial deflection when arranged as an unloaded beam. The specimen having been inserted above the rollers 34, 36 it also passes beneath the nose roller 46. The test of bending stiffness may then be begun by lowering the anvil until the lower surface of the nose roller 46 contacts the upper surface of the specimen "S" at or near the center thereof. At this point, a series of successive readings is taken and/or recorded. As is known to those skilled in the art, the test apparatus or tensiometer is arranged in such a way that the crosshead 38 of the machine is raised by the operation of jack screws concealed within the left and right hand uprights 40, 42. During continued movement, a continuous record is made and kept of the forces applied to the load cell 20. This is continued until sufficient bending has been achieved to make a reliable force/deflection curve for the test specimen being evaluated. In FIG. 1, the tensiometer is generally designated 8 and is shown to include an instrument board generally designated 44 having plural windows 46 for displaying readings, as well as a keyboard generally designated 48 for machine control, i.e., advance sped, rest points, etc. The tensiometer having this arrangement is conventional and not a part of the invention. It is not believed that further description is required for an understanding of the present invention.

Referring now to an important advantage of the invention, as pointed out above, testing surface-soft materials with conventional fixtures has created erratic and unreliable readings. While the present invention does not depend for its success upon the application for any particular theory or mode of operation, it is believed that surface-soft materials, when supported on knife edges, points, flat bars or the like (which are fully acceptable for measuring bending stiffness of rigid, surface-hard or slippery surfaced materials) are not satisfactorily tested with such fixtures.

However, where a material undergoes not only bending upon application of a beam load, it also tends to undergo extension. If the test fixture "grabs" or becomes embedded in the surface, it does not allow the specimen surface to slide past the portion of the mounting fixture engaged by the specimen. The consequences of this are that a portion of the perceived resistance to bending is actually resistance in tension, inasmuch as the specimen is effectively being gripped and extended in tension, rather than simply in bending. If this phenomenon is transient, which is the best case, then the readings made are simply erratic. However, if the condition persists throughout the test, then seriously erroneous readings can be generated. By the simple expedient of using the test fixture of the invention, this difficulty with prior art testing can easily be overcome.

The recent increase in use of rubber as a structural component of composite structures has caused an increased need for accurate measurement of the properties of rubber specimens. Such measurements are important in the sealing industry, where not only surface contact, but also the ability to apply to a radial load or to respond to runout or other irregularities is important. In other cases, rubber used as a structural or semi-structural element exclusive of the sealing function, and proper engineering is dependent upon making accurate readings of test measurements on test specimens. With the advent of sophisticated testing machines and improved instrumentation, the advantages able to be realized achieve even greater significance. The present invention provides a simple, economical fixture for measuring deflection under load with great accuracy under the conditions described.

It will thus be seen that the present invention provides an improved test fixture for determining the stiffness in bending and other properties of surface-soft materials, such as elastomers and like products. The preferred form of invention having been described by way of example, it is anticipated that modifications and changes to the described form of apparatus will occur to those skilled in the art, and it is anticipated that such changes may be made without departing from the spirit of the invention or the scope of the appended claims.

What is claimed is:

1. An apparatus for measuring the bending stiffness of a specimen of flexible material with a soft exterior surface, said apparatus adapted for mounting and use in a tensiometer and comprising, in combination, A yoke member having a crosspiece and two pairs of spaced, apart, complementary legs, means for attaching said crosspiece to a first, relatively movable element of a tensiometer, and each of said leg pairs depending from said crosspiece and each including means for retaining an end of an associated specimen support roller therein, a specimen support roller for each pair of legs, each of said specimen support rollers being cylindrically shaped and substantially circular in cross-section and each having end portions rotatably disposed within said retaining means, said support rollers being arranged substantially parallel to and spaced apart from each other by a given distance and providing support surfaces to support the lower surface of a specimen of flexible material within the apparatus, an anvil member including a crosspiece, means for attaching said crosspiece to a second, relatively movable element of a tensiometer, and a pair of spaced apart legs extending from said crosspiece, with each of said legs also including means for mounting specimen-engaging means in the form of a nose roller extending between said legs, said anvil member being positionable relative to said yoke member such that said nose roller lies parallel to and midway between said support members;

said nose roller being adapted to engage the upper surface of said specimen, said specimen being subject to bending when said yoke and anvil rollers respectively move vertically apart with respect to one another.

2. An apparatus as defined in claim 1 wherein said respective pairs of legs retaining said support rollers on said yoke member are arranged in an inverted "V" configuration relative to each other, whereby said specimen rollers are spaced apart from each other a distance greater than the width of said crosspiece.

3. An apparatus as defined in claim 2 wherein said pairs of legs forming said "V" configuration lie in planes perpendicular to said crosspiece.

4. An apparatus as defined in claim 1 wherein said means for retaining said end of said support roller relative to said legs on said yoke member comprises an opening in each of said legs, each of said openings including an insert bushing made from a low friction material.

5. An apparatus as defined in claim 1 wherein said spaced apart legs forming a part of said anvil are of generally triangular form in elevation.

6. An apparatus as defined in claim 1 wherein each of said spaced apart legs forming a part of said anvil includes an opening comprising said mounting means, said mounting means further including a bushing made from a low friction material, inserted within said opening.

7. An apparatus for measuring the bending stiffness of a specimen of flexible material with a soft exterior surface, said apparatus adapted for mounting and use in a tensiometer and comprising, in combination, A yoke member having a crosspiece and two pairs of spaced, apart, complementary legs, means for attaching said crosspiece to a first, relatively movable element of a tensiometer, and each of said leg pairs depending from said crosspiece and each including means for retaining an end of an associated specimen support roller therein, said retaining means including an opening in each of said legs and an insert bushing made of a low friction material and inserted into each of said openings in said legs, a specimen support member for each pair of legs, each of said specimen support rollers being cylindrically shaped and substantially circular in cross-section and each having end portions rotatably disposed within said retaining means, said support rollers being arranged substantially parallel to and spaced apart from each other by a given distance, an anvil member including a crosspiece, means for attaching said crosspiece to a second, relatively movable element of a tensiometer, and a pair of spaced apart legs extending from said crosspiece, with each of said legs also including means for mounting specimen-engaging means in the form of a nose roller extending between said legs, said anvil member being positionable relative to said yoke member such that said nose roller lies parallel to and midway between said support members;

said yoke support rollers being adapted to engage and support the lower surface of said specimen and said nose roller being adapted to engage the upper surface of said specimen, said specimen being subject to bending when said yoke and anvil rollers move vertically apart with respect to one another.

8. An apparatus as defined in claim 7 wherein said respective pairs of legs retaining said support rollers on said yoke member are arranged in an inverted "V" configuration relative to each other, whereby said specimen rollers are spaced apart from each other a distance greater than the width of said crosspiece.

9. An apparatus as defined in claim 8 wherein said pairs of legs forming said "V" configuration lie in planes perpendicular to said crosspiece.

10. An apparatus as defined in claim 7 wherein said spaced apart legs forming a part of said anvil are of generally triangular form in elevation.

11. An apparatus as defined in claim 7 wherein each of said spaced apart legs forming a part of said anvil includes an opening comprising said mounting means, said mounting means further including a bushing made from a low friction material, inserted within said opening.

12. An apparatus for measuring the bending stiffness of a specimen of flexible material with a soft exterior surface, said apparatus adapted for mounting and use in a tensiometer and comprising, in combination, A yoke member having a crosspiece and two pairs of spaced, apart, complementary legs, means for attaching said crosspiece to a first, relatively movable element of a tensiometer, and each of said leg pairs depending from said crosspiece and each including means for retaining an end of an associated specimen support roller therein, a specimen support roller for each pair of legs, each of said specimen support rollers being cylindrically shaped and substantially circular in cross-section and each having end portions rotatably disposed within said retaining means, said support rollers being arranged substantially parallel to and spaced apart from each other by a given distance, an anvil member including a crosspiece, means for attaching said crosspiece to a second, relatively movable element of a tensiometer, and a pair of spaced apart legs extending from said crosspiece, with each of said legs also including means for mounting specimen-engaging means in the form of a nose roller extending between said legs, said mounting means comprising an opening in each of said legs and a bushing made from a low friction material mounted within each said opening, said anvil member being positionable relative to said yoke member such that said nose roller lies parallel to and midway between said support members;

said yoke support rollers being adapted to engage and support the lower surface of said specimen and said nose roller being adapted to engage the upper surface of said specimen, said specimen being subject to bending when said yoke and anvil rollers respectively move vertically apart with respect to one another.

13. An apparatus as defined in claim 12 wherein respective pairs of legs retaining said support rollers on said yoke member are arranged in an inverted "V" configuration relative to each other, whereby said specimen rollers are spaced apart from each other a distance greater than the width of said crosspiece.

14. An apparatus as defined in claim 13 wherein said pairs of legs forming said "V" configuration lie in planes perpendicular to said crosspiece.

15. An apparatus as defined in claim 12 wherein said means for retaining said end of said support roller relative to said legs on said yoke member comprises an opening in each of said legs, each of said openings including an insert bushing made from a low friction material.

16. An apparatus as defined in claim 12 wherein said spaced apart legs forming a part of said anvil are of generally triangular form in elevation.

* * * * *